United States Patent
Aleti (10) Patent No.: US 11,187,419 B2
(45) Date of Patent: Nov. 30, 2021

(54) SYSTEM AND METHOD FOR EFFICIENT, AMBIENT AIR PURIFICATION

(71) Applicant: PRAMUKHA TECHNOLOGIES PVT. LTD, Hyderabad (IN)

(72) Inventor: Anil Kumar Aleti, Hyderabad (IN)

(73) Assignee: PRAMUKHA TECHNOLOGIES PVT. LTD., Hyderabad (IN)

( * ) Notice: Subject to any disclaimer, the term of this patent is extended or adjusted under 35 U.S.C. 154(b) by 391 days.

(21) Appl. No.: 16/326,771

(22) PCT Filed: Dec. 12, 2016

(86) PCT No.: PCT/IB2016/057529
§ 371 (c)(1),
(2) Date: Feb. 20, 2019

(87) PCT Pub. No.: WO2018/109522
PCT Pub. Date: Jun. 21, 2018

(65) Prior Publication Data
US 2019/0203959 A1    Jul. 4, 2019

(51) Int. Cl.
*F24F 3/16*        (2021.01)
*F24F 11/30*      (2018.01)
(Continued)

(52) U.S. Cl.
CPC ............... *F24F 3/16* (2013.01); *F24F 11/30* (2018.01); *F24F 11/64* (2018.01); *G01N 33/004* (2013.01);
(Continued)

(58) Field of Classification Search
CPC . A23L 3/3409; A61L 2/20; B01J 19/08; B01J 19/12; F24F 11/30; F24F 11/64;
(Continued)

(56) References Cited

U.S. PATENT DOCUMENTS

| | | | | |
|---|---|---|---|---|
| 4,432,062 A | * | 2/1984 | Herklotz | B03C 3/763 95/26 |
| 5,711,785 A | * | 1/1998 | Maxwell | B01D 46/0068 95/15 |
| 6,332,917 B1 | * | 12/2001 | Schollkopf | F15B 1/26 55/DIG. 17 |
| 7,875,099 B2 | * | 1/2011 | Abraham | G06F 1/206 95/4 |

(Continued)

FOREIGN PATENT DOCUMENTS

WO    2016/040954 A2    3/2016

OTHER PUBLICATIONS

Mead, et al. "The use of electrochemical sensors for monitoring urban air quality in low-cost, high density networks." Atmospheric Environment [online], May 2013 [Retrieved on Jan. 10, 2018], vol. 70, pp. 186-203, [Retrieve from URL: https://doi.org/10.1016/j.atmosenv.2012.11.060>, Abstract only.

*Primary Examiner* — Minh Chau T Pham
(74) *Attorney, Agent, or Firm* — United IP Counselors, LLC (57) ABSTRACT

The present invention is an energy efficient air purification system 100 for purifying a complex polluted environmental air condition. The air purification system 100 includes a plurality of air pollution monitoring units $MU_1$, $MU_2$, $MU_3$, $MU_4$ . . . $MU_N$ which are installed at distant locations, a plurality of air purification units $PU_1$, $PU_2$, $PU_3$, $PU_4$ . . . $PU_N$ which are installed at distant locations and an automated control unit 500. The air pollution monitoring units are adapted to monitor the quality of the air in their surroundings. Upon such monitoring, the air pollution monitoring units are adapted to communicate the air quality data to the automated control unit 500. The automated control unit 500 is adapted to analyze the air quality data and on basis of such analysis, the automated control unit 500 further instructs the air purification units for further action.

20 Claims, 7 Drawing Sheets

(51) Int. Cl.
*G01N 33/00* (2006.01)
*F24F 11/64* (2018.01)
*F24F 8/108* (2021.01)
*F24F 8/117* (2021.01)
*F24F 8/167* (2021.01)
*F24F 8/183* (2021.01)
*F24F 8/192* (2021.01)

(52) U.S. Cl.
CPC ..... *G01N 33/0031* (2013.01); *G01N 33/0037* (2013.01); *G01N 33/0042* (2013.01); *G01N 33/0063* (2013.01); *F24F 8/108* (2021.01); *F24F 8/117* (2021.01); *F24F 8/167* (2021.01); *F24F 8/183* (2021.01); *F24F 8/194* (2021.01)

(58) Field of Classification Search
CPC ............. G01N 33/0031; G01N 33/004; G01N 33/0037; G01N 33/0042; G01N 33/0063

USPC ............. 55/385.1, 385.2, 467, 473, DIG. 34; 95/4, 14, 17, 57, 273; 96/19, 63, 407, 96/417, 420
See application file for complete search history.

(56) References Cited

U.S. PATENT DOCUMENTS

| | | | |
|---|---|---|---|
| 8,328,905 B2* | 12/2012 | Matsuzaki | B01D 46/0086 95/25 |
| 9,597,620 B2* | 3/2017 | Verdegan | G06Q 10/06 |
| 10,222,077 B2* | 3/2019 | Takei | F24F 8/10 |
| 2009/0185959 A1* | 7/2009 | Weber | C01B 13/11 422/107 |
| 2016/0266081 A1* | 9/2016 | Risk | G01D 18/008 |
| 2016/0370338 A1* | 12/2016 | Sayfan | G01N 33/0062 |

* cited by examiner

A- TOP VIEW

SYSTEM AND METHOD FOR EFFICIENT, AMBIENT AIR PURIFICATION

FIELD OF THE DISCLOSURE

The field of the present invention relates generally to an energy efficient air purification system. More specifically, the present invention provides a system and method for purifying a complex polluted environmental air condition and releasing the clean air into the atmosphere.

BACKGROUND OF THE DISCLOSURE

Since last few decades, air pollution has been a major concern and has been a topic of serious discussion to the mankind. Whether it is the pollution on the roads caused by vehicles or pollution caused by the industrial exhaust gases, the overall air pollution is causing serious harm to human beings as well as animals. It is well known that various hazardous gaseous compounds are released from automobiles, fireplaces, industries, gas stoves, space heaters, chimneys, chemical industries and faulty furnaces. All these hazardous gaseous compounds are posing a significant air pollution problem in major cities.

Ambient or atmospheric air pollution is harmful for the flora and fauna. The major problem is difficulty of getting fresh and clean air for plants as well as for animals. It is known from WHO (World Health Organization) studies that for human beings, respiratory illnesses such as Bronchitis, Asthma, and lung cancer are caused if excessive pollutants are present in the atmosphere.

Of late, in both developed and developing countries sustainable development has emerged as a priority. One of the ways to sustain clean atmosphere for future generations is to treat air pollutants and industrial effluents before they are released into the atmosphere. Worldwide, various standards are being prescribed such as BS-IV (Bharat Stage emission standards), and Euro-VI (European Emission Standards) to limit the air pollutants being released into the atmosphere by the automobile vehicles.

However, there is a limit to which flue gases can be treated in the industrial context. Similarly, despite advancements in the catalytic converter technology for meeting various emission norms (Euro-VI, etc.), as the number of automobiles increases, the 'remnant pollutants' such as particulates are still released into the atmosphere. The catalytic converter principally targets NOx and SOx gases for emission control. Solid particulate matter such as PM2.5 and PM10 (particulate matter less than 2.5 and 10 microns respectively) are still released into the atmosphere even after emission treatment. The problem is particularly vexing in the case of diesel vehicles. As a result, several countries like Brazil, India, Italy, and UK are experimenting with limitations on vehicle population on the road.

In a recent report by WHO, of the top 20 most polluted cities in the world, 13 are in India. Hence, an invention which aims to reduce air pollution of the external atmosphere is the need of the hour. It is surmised that in the future, CNG vehicles may gradually replace the diesel vehicles in India (which are relatively more polluting). However, the timeline to achieve such a goal may be several years away. Moreover, dust is another pollutant in cities which contributes considerably as one of the factors to increase particulate matter in a given ecosystem of a city.

There are many devices available in the market for purification of internal polluted air and industrial gaseous effluents. However, purifying and cleaning atmospheric polluted air and releasing fresh and clean air into the atmosphere which is close to the general public is still a matter of concern. There is a need for such a system which not only purifies the air, but also releases the clean air into the atmosphere which is rich in oxygen and other essential components.

SUMMARY OF THE DISCLOSURE

In view of the foregoing disadvantages inherent in the current generally known air purification systems and the needs as mentioned above, the general purpose of the present disclosure is to provide an energy efficient air purification system that is configured to include all advantages of the known air purification systems and to overcome the drawbacks inherent in the prior art, offering some added advantages.

To achieve the above objectives and to fulfill the identified needs, in one aspect, the present invention provides an energy efficient air purification system for purifying a complex polluted environmental air condition. The said air purification system comprises a plurality of air pollution monitoring units which are installed at distant locations. Each of the said plurality of air pollution monitoring units is adapted to monitor the air quality of its surrounding location. The said air purification system also includes a plurality of air purification units which are installed at distant locations such that each of the said plurality of air purification units are adapted to purify the polluted air of its surrounding location, with a split design of purification units and their suction and discharge air vents. Further, the air purification system also includes an automated control unit which is in communication with the said plurality of air pollution monitoring units and the said plurality of air purification units. The said automated control unit provides a means of remotely controlling the working of the said plurality of air purification units including instrumentation units and actuation systems.

In an aspect of the present invention, the air pollution monitoring unit comprises at least an air pollutant detector adapted to detect the level of various air pollutants, a processor adapted to process the data of the said air pollutant detector into a message format and a communication interface having a transceiver adapted to transmit the said message format to the said automated control unit.

In an aspect of the present invention, the air purification unit comprises at least an air cleaning component adapted to filter at least an air pollutant and a controller working in communication with the said automated control unit, wherein the said controller is adapted to control the functionality of each of the said plurality of air purification units.

In an aspect of the present invention, air cleaning component is selected from air filtration components such as wet scrubber, an electrostatic precipitator, a particulate filter, a catalytic filter, a cyclonic separator, a baghouse collector.

In an aspect of the present invention, the automated control unit comprises a receiver component, a memory component, a processor component, and a transmitter component.

In another aspect of the present invention, the receiver component is adapted to receive the said message format from the said communication interface.

In yet another aspect of the present invention, the memory component is adapted to store a preset clean air data of a specific location, and a historical air quality data of a specific location.

In yet another aspect of the present invention, processor component comprises a data decoder adapted to decode the said message format into a data format and an analyzer module adapted to analyze the said data format in relation with the said preset clean air data of the specific location, wherein the analyzer module generates a command as per the said data analysis. The said command is communicated to efficiently operate the said plurality of air purification units.

This together with the other aspects of the present invention along with the various features of novelty that characterized the present disclosure is pointed out with particularity in claims annexed hereto and forms a part of the present invention. For better understanding of the present disclosure, its operating advantages, and the specified objective attained by its uses, reference should be made to the accompanying descriptive matter in which there are illustrated exemplary embodiments of the present invention.

BRIEF DESCRIPTION OF THE DRAWINGS

The advantages and features of the present disclosure will become better understood with reference to the following detailed description and claims taken in conjunction with the accompanying drawings, in which:

Like numerals refer to like elements throughout the present disclosure.

DETAILED DESCRIPTION OF THE DISCLOSURE

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

The terms "a" and "an" herein do not denote a limitation of quantity, but rather denote the presence of at least one of the referenced item.

The terms "having", "comprising", "including", and variations thereof signify the presence of a component.

The present invention relates to an energy efficient air purification system for purifying a complex polluted environmental air condition. More specifically, the present air purification system is capable of being installed in an open area, at traffic junctions, at bus stops, or at places where there is more concentrated air pollution in the atmosphere. The present air purification system is capable of sucking in the polluted air, filtering, purifying and releasing clean air into the atmosphere. Such equipment of the air purification system capable of release of purified air is installed in areas where there is more concentration of general public, pedestrians etc. The said energy efficient air purification system shall now be explained in conjunction with all the FIGS. 1-6 of this document.

Figure 1:
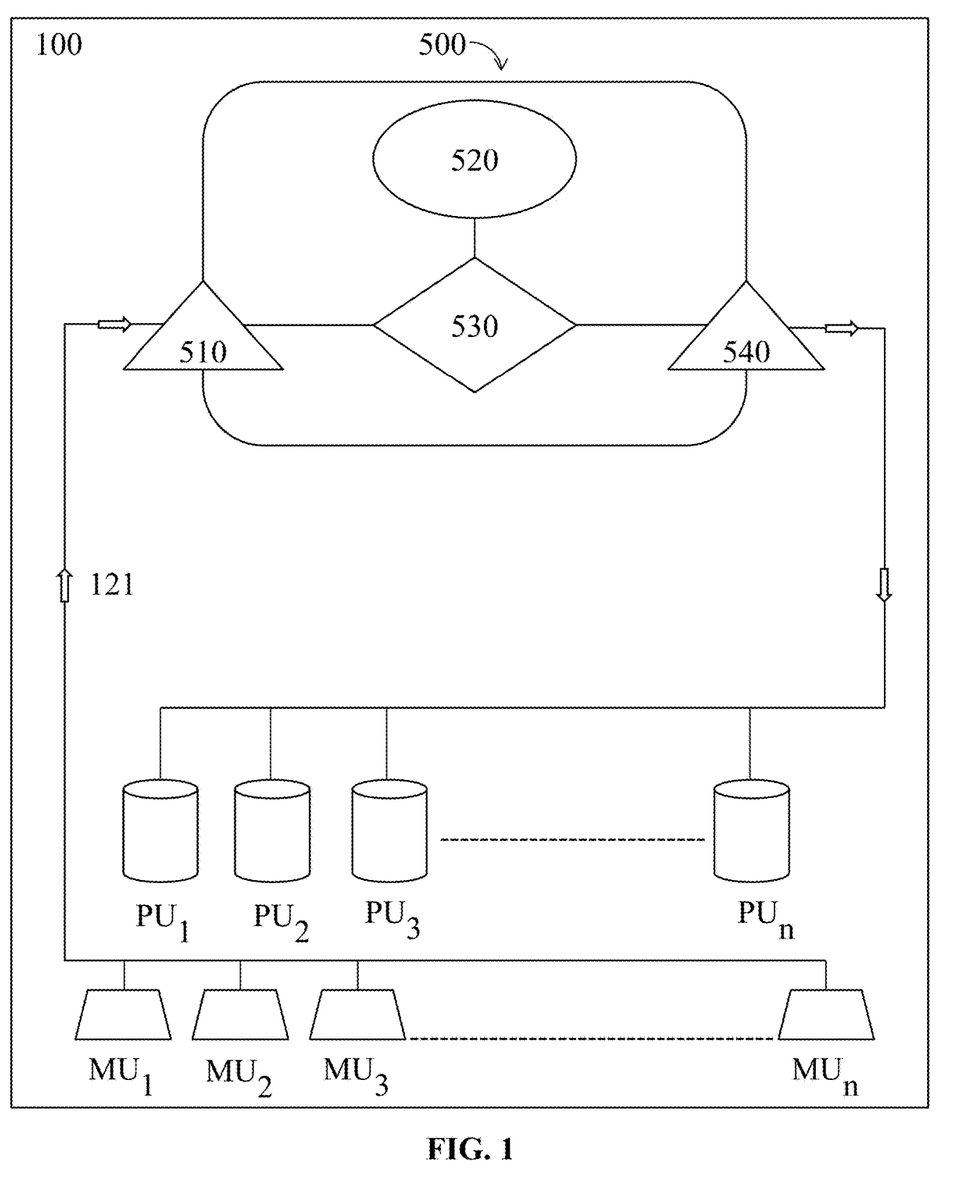
FIG. 1 illustrates a conceptual block diagram of the working of various components of the energy efficient air purification system, according to various embodiments of the present invention.

Referring to FIG. 1 of the accompanying drawings, there is shown a block diagram illustrating the working mechanism for the air purification device. There are shown a plurality of air pollution monitoring units $MU_1$, $MU_2$, $MU_3$, $MU_4$ ... $MU_N$ and a plurality of air purification units $PU_1$, $PU_2$, $PU_3$, $PU_4$ ... $PU_N$. The air pollution monitoring units $MU_1$, $MU_2$, $MU_3$, $MU_4$ ... $MU_N$ are capable of monitoring the quality of air in their surrounding locations. The said air pollution monitoring units $MU_1$, $MU_2$, $MU_3$, $MU_4$ ... $MU_N$ are installed at distant locations from each other so that they cover a larger area for monitoring the air quality of the atmosphere. The construction and configuration of the air pollution monitoring units $MU_1$, $MU_2$, $MU_3$, $MU_4$ ... $MU_N$ will be explained later with reference to FIG. 3A.

In an embodiment, the air pollution monitoring units $MU_1$, $MU_2$, $MU_3$, $MU_4$ ... $MU_N$ are adapted to monitor the air quality in their respective surrounding locations and communicate that information to an automated control unit 500. The automated control unit 500 is communicably coupled to the air pollution monitoring units $MU_1$, $MU_2$, $MU_3$, $MU_4$ ... $MU_N$ and the air purification units $PU_1$, $PU_2$, $PU_3$, $PU_4$ ... $PU_N$. Moreover, the automated control unit 500 is adapted to control the functioning of the air purification units $PU_1$, $PU_2$, $PU_3$, $PU_4$ ... $PU_N$, by utilizing instrumentation and actuation mechanism within $PU_1$, $PU_2$, $PU_3$, $PU_4$ ... $PU_N$.

In an embodiment of the present invention, the automated control unit 500 is located centrally at a particular location and is configured to control a plurality of air purification units $PU_1$, $PU_2$, $PU_3$, $PU_4$ ... $PU_N$ which are typically installed over a wide area.

In another embodiment of the present invention, the automated control unit 500 is installed with each of the air pollution monitoring units $MU_1$, $MU_2$, $MU_3$, $MU_4$ ... $MU_N$.

As shown in FIG. 1, the automated control unit 500 comprises a receiver component 510, a memory component 520, a processor component 530, and a transmitter component 540.

In an embodiment, as shown in FIG. 1, the receiver component 510 is adapted to receive message from the air pollution monitoring units $MU_1$, $MU_2$, $MU_3$, $MU_4$ ... $MU_N$, the received message being in a specific format.

In an embodiment, the processor component 530 comprises a data decoder which is adapted to decode the message format into a data format and an analyzer module adapted to analyze the said data format in relation with a preset clean air quality data of a specific location. The analyzer module comprises a set of instructions for generating a command on the basis of the data analysis when received data is compared with the preset clean air quality data of a specific location. Said generated command is then transmitted by the transmitter component 540 to the air purification units $PU_1$, $PU_2$, $PU_3$, $PU_4$ ... $PU_N$.

Figure 3A:
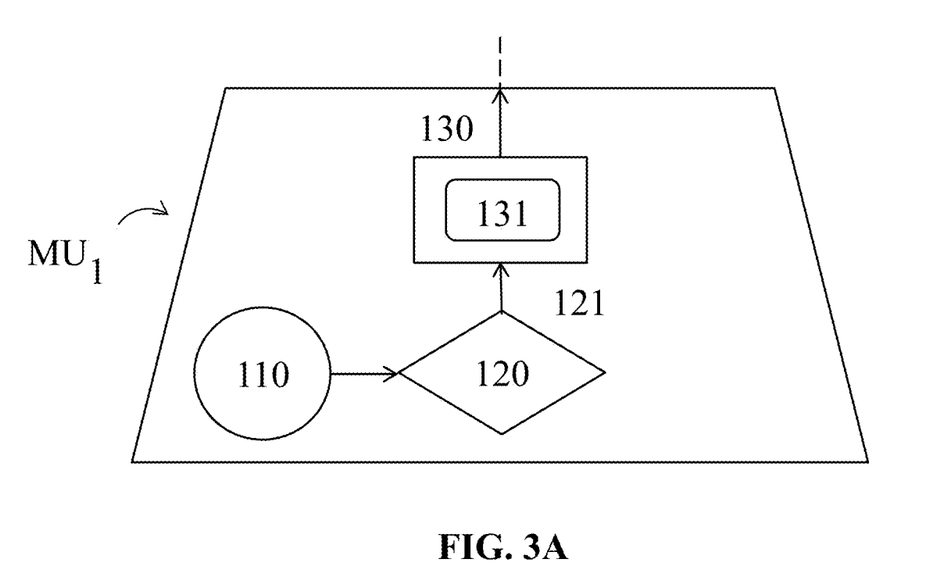
FIG. 3A illustrates a conceptual block diagram providing the configuration of the air pollution monitoring unit according to various embodiments of the present invention.

According to FIG. 3A, there is shown a block diagram for the construction of the plurality of air pollution monitoring units $MU_1$, $MU_2$, $MU_3$, $MU_4$ ... $MU_N$. Each of the air pollution monitoring unit comprises at least an air pollutant detector 110 which is adapted to detect the level of various air pollutants, a processor 120 adapted to process the data of the said air pollutant detector into a message format 121 and a communication interface 130 having a transceiver 131 adapted to transmit the said message format 121 to the automated control unit 500.

It will be apparent to a person skilled in the art that the air pollutant detector 110 is an electronic device such as a gas analyzer/detector which is capable of sensing and detecting various pollutants in the surrounding atmosphere. The pollutants responsible for polluting the air may comprise particulate matter, carbon monoxide, sulfur dioxide, nitrous oxide and the like. The particulate matters may further vary in their sizes.

Once the air pollutant detector detects the levels of pollutants, this data is communicated to the processor 120 which is adapted to convert this data into a predefined message format 121.

Thereafter, the said data in the predefined message format 121 is forwarded to the communication interface 130 which has a transceiver 131 for transmitting the message format to the automated control unit 500. At the end of the automated control unit 500, the receiver component 510 is adapted to receive the message format 121 transmitted by the transceiver 131.

In a preferred embodiment of the present invention, the air pollutant detector 110 is an air particulate matter detector which is capable of detection of PM2.5 and PM10 particulate matters. In this embodiment, the air purification units $PU_1$, $PU_2$, $PU_3$, $PU_4$ ... $PU_N$ are only capable of purifying these particulate matter PM2.5 and PM10. In each of these air purification units $PU_1$, $PU_2$, $PU_3$, $PU_4$ ... $PU_N$, the air purification component is a set of bag filters (baghouses) or Fabric Filters, which are capable of removing the Particulate pollutants at nearly 99 percent particulate collection efficiency.

In another preferred embodiment of the present invention, the air pollutant detector 110 is a gaseous atmospheric pollutant detector which is capable of detection of particulate matter (PM2.5, PM10), $NO_x$ (Nitrogen Oxides), $SO_x$ (Sulfur Oxides), Hg (Mercury), Organic HAPs (Hazardous Air Pollutants), CO (Carbon Monoxide). A nano-catalytic filter is used in the air purification units $PU_1$, $PU_2$, $PU_3$, $PU_4$ ... $PU_N$ to filter all the above pollutants with a high degree of efficiency and at a lower temperature compared to other conventional catalytic filtration processes.

Figure 3B:
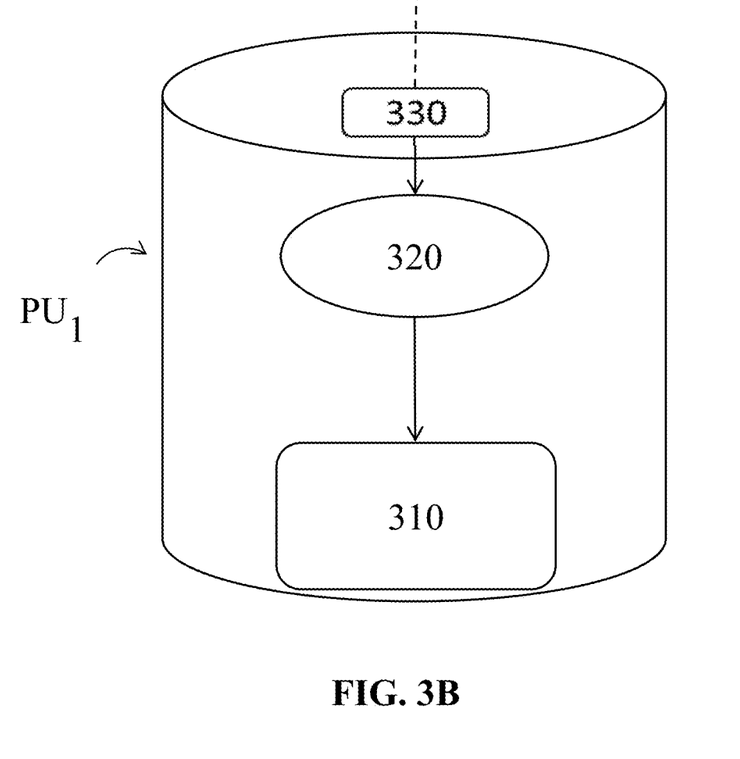
FIG. 3B illustrates a conceptual block diagram providing the configuration of the air purification unit according to various embodiments of the present invention.

Referring now to FIG. 3B, there is shown a constructional architecture for the one of the plurality of air purification units $PU_1$, $PU_2$, $PU_3$, $PU_4$ ... $PU_N$. Each of the air purification units $PU_1$, $PU_2$, $PU_3$, $PU_4$ ... $PU_N$ comprises at least one air cleaning component 310 and a controller 320 which is adapted to control the entire air purification unit $PU_1$. Furthermore, there is provided an air pressure controlling unit 330 in each of the air purification units, wherein the said air pressure controlling unit 330 is adapted to control the pressure of the air flowing to the air purification component 310 for purification. The controller 320 is communicably coupled to the air cleaning component 310 and the air pressure controlling unit 330.

In an embodiment, the air cleaning component 310 is adapted to filter an air pollutant from the polluted air. It will be obvious to a person skilled in the art that an air pollutant may be any kind of pollutant such as particulate matter, carbon monoxide, sulfur dioxide, nitrous oxide and the like. The air cleaning component 310 of the present invention is also capable of filtering particulate matters of size 2.5 microns and smaller PM2.5 and particulate matter of size 10 microns and smaller PM10.

In an embodiment of the present invention, the air cleaning component 310 is selected from air filtration components such as one of a wet scrubber, an electrostatic precipitator, a particulate filter, a catalytic filter, a cyclonic separator or a baghouse collector.

The air cleaning component 310 is capable of filtering out the air pollutants from the polluted air and thereby cleaning the air.

In an exemplary embodiment of the present invention, the air cleaning component 310 is a baghouse collector. Baghouse collectors are air filtration devices which use fabric filter tubes, envelopes, or cartridges to capture or separate dust and other particulate matter (PM). These baghouse collectors include bags suspended inside a housing or casing. Once the polluted air is fed inside the housing, the suspended bags capture the particulate matter and allow formation of a layer of particulate matter on its surface. Once the particulate matter is layered on the outer surface of the suspended bags, the remaining air which is pure is sent out through the outlet vents.

The controller 320 is adapted to receive command from the transmitter component 540 of the automated control unit 500.

In an embodiment of the present invention, the controller 320 is adapted to activate the air purification unit $PU_1$ when it receives command from the transmitter component 540 of the automated control unit 500. The said command is generated when the air pollutant detector 110 belonging to each of the air pollution monitoring units $MU_1$, $MU_2$, $MU_3$, $MU_4$ ... $MU_N$ detect the level of air pollutants in their surrounding locations and then that data is further formatted and transmitted to the automated control unit 500. At the end of the automated control unit 500, the processor component 530 is adapted to check or compare the said data with the preset clean air quality data of that particular location.

In an embodiment, if the said comparison or analysis of data with the preset clean air data indicates poor quality of air, this is an indication that the air in the surrounding location with respect to one of the plurality of air pollution monitoring units $MU_1$, $MU_2$, $MU_3$, $MU_4$ ... $MU_N$ is contaminated and requires immediate purification. The criteria for such analysis of data shall be explained in more detail with reference to FIGS. 2A and 2B.

In scenarios such as above, the automated control unit 500 immediately notifies the respective air purification unit from among the plurality of air purification units $PU_1$, $PU_2$, $PU_3$, $PU_4 \ldots PU_N$ to start the air purification procedure (defined in FIG. 2A, 2B) in that particular location.

Generally, the surrounding location in scope for purification is considered within a radius of 1 km from the physical installation of the one of the plurality of air purification units $PU_1$, $PU_2$, $PU_3$, $PU_4 \ldots PU_N$. This however, should not be construed as a limitation of the present invention, the radius of the surrounding location may vary and the air purification units may further be configured to cover a larger and bigger area for purification of air.

Figure 2A:
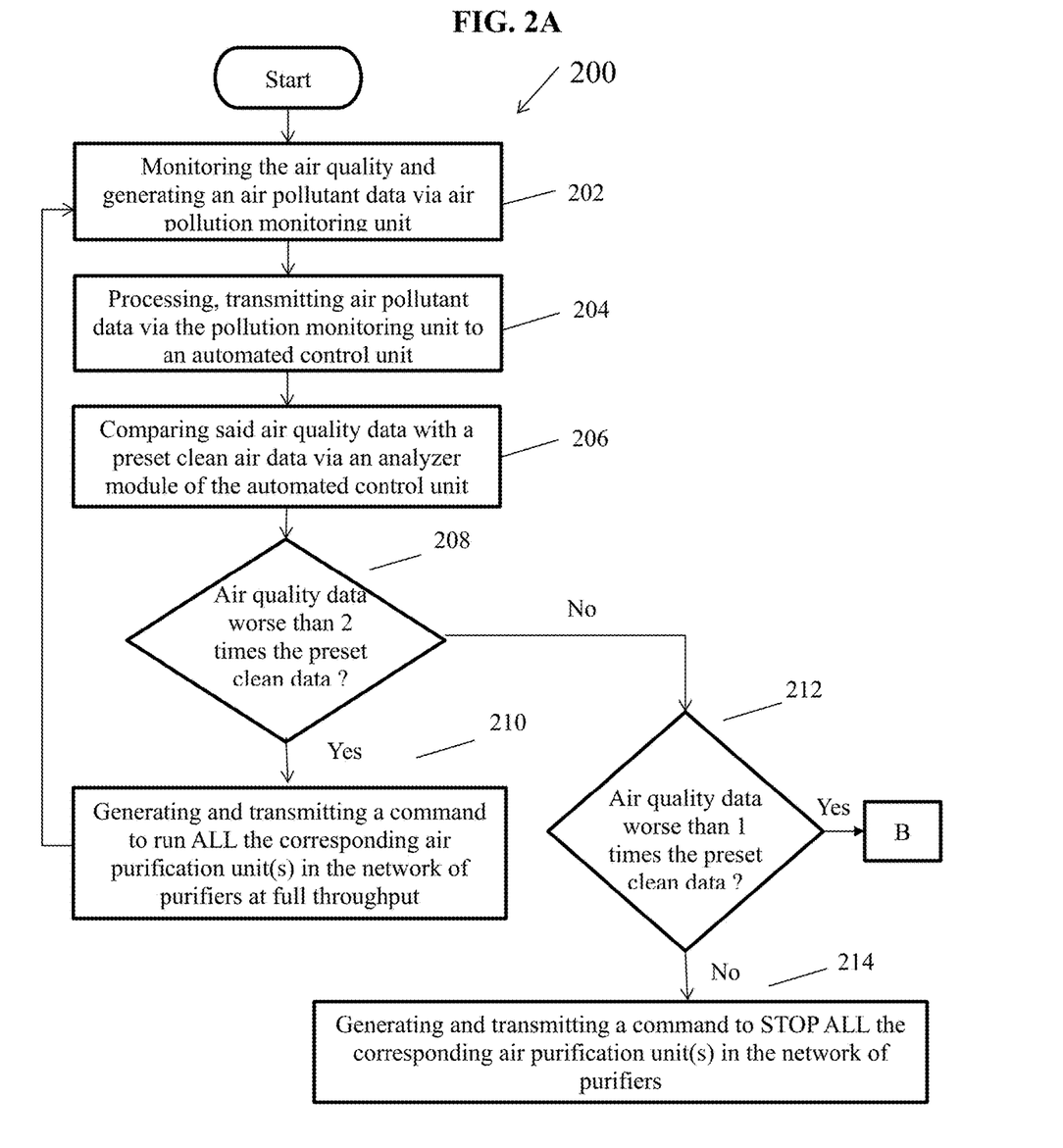
FIGS. 2A and 2B provide flowcharts for the working of the energy efficient air purification system, according to various embodiments of the present invention.
Figure 2B:
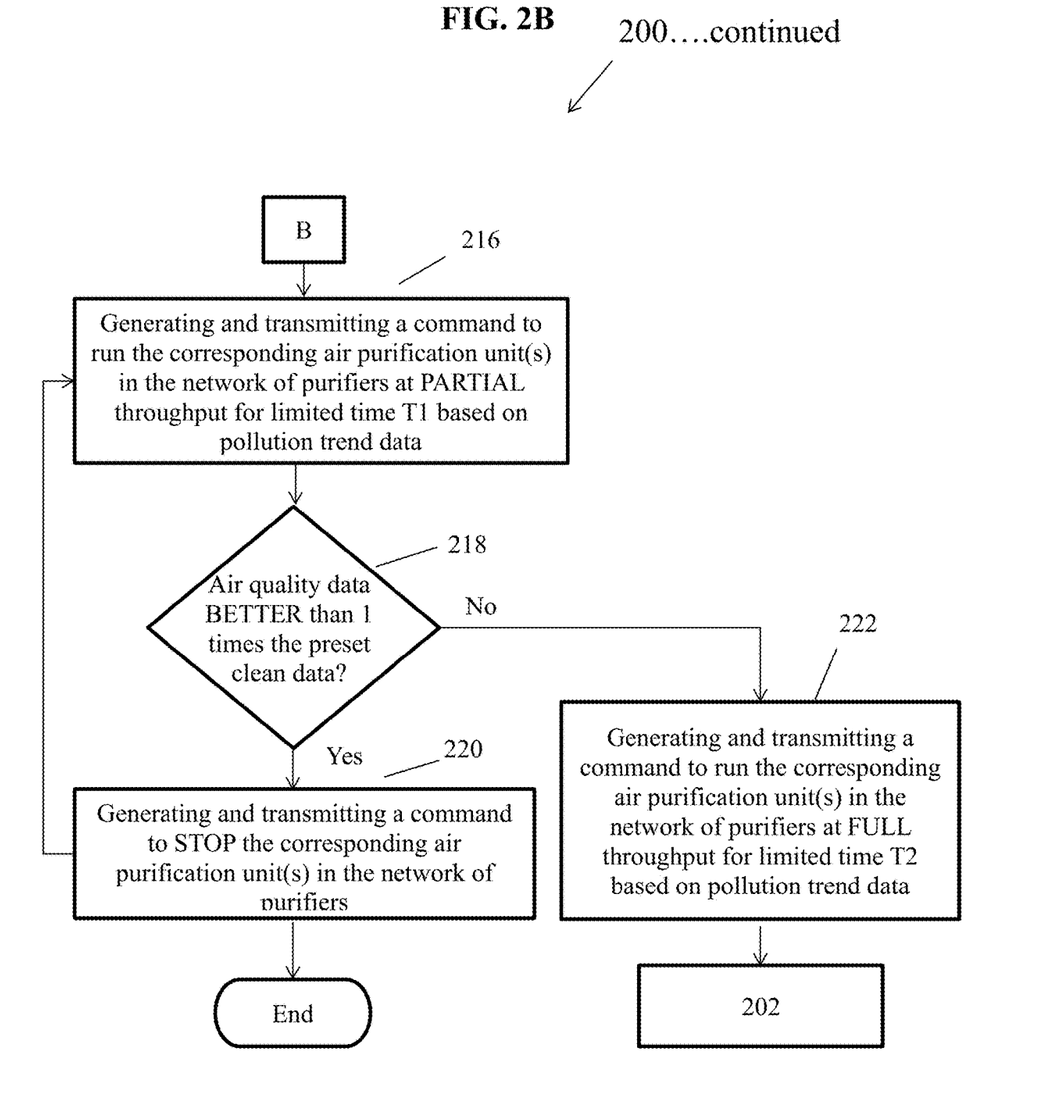

Referring now to FIGS. 2A and 2B, there is shown a flowchart with respect to the functioning of the air purification system 100. There is shown a method 200 which begins at step 202. At this step 202, the system 100 is adapted to monitor the air quality in a surrounding location. The consistent monitoring of the air quality in surrounding location is performed by the air pollution monitoring units $MU_1$, $MU_2$, $MU_3$, $MU_4 \ldots MU_N$ in their respective surrounding locations.

These air pollution monitoring units $MU_1$, $MU_2$, $MU_3$, $MU_4 \ldots MU_N$ are physically installed at various locations at specific distance from each other so that each of these units can monitor air quality in their surrounding locations and thereby covering a larger area for air purification. The number of these units in some embodiments maybe larger than the number of Air Purification Units $PU_1$, $PU_2$, $PU_3$, $PU_4 \ldots PU_N$ in order to fulfil operational requirements or increase efficiency.

While monitoring the air quality, the air pollutant detector 110 of the air pollution monitoring units $MU_1$, $MU_2$, $MU_3$, $MU_4 \ldots MU_N$ detects the level of various air pollutants in the surrounding air, thereby generating an air pollutant data.

At step 204, the air pollutant data is further converted to a specific message format by a processor component 120 of each of the air pollution monitoring units $MU_1$, $MU_2$, $MU_3$, $MU_4 \ldots MU_N$. Once the air pollutant data is converted to a specific message format 121, it is ready for transmission to the automated control unit 500. The said message format 121 is transmitted via the communication interface 130 to the automated control unit 500.

On receipt of the message format 121 at the automated control unit 500, the message format 121 is decoded into a data format by a data decoder integrated within the processor component 530 of the automated control unit. In the said processor component 530, there is provided an analyzer module which is configured to analyze the said data format and compare it with the preset clean air data at step 206 of the method 200.

It will be obvious to a person skilled in the art that the preset clean air data is predetermined when the air contained far too less quantity of air pollutants and which was considered to be healthy and safe for breathing of the living beings.

The preset clean air data can comprise information such as permitted level of pollutants like PM2.5, PM10, Carbon Monoxide, Sulphur Oxides, Nitrogen Oxides, particulate matters etc. which implies that the air was supposedly considered to be clean and fit for human breathing.

Moving further to step 208, the analyzer module of the processor component 530 is adapted to compare/analyze the air quality data with the preset clean air quality data. The analyzer is adapted to check if the air quality data is worse than 2 times the preset clean air quality data. If the comparison confirms that the air quality data is worse than 2 times the preset clean air quality data, then the method moves to step 210. The analyzer module of the processor component 530 of the automated control unit 500 is adapted to generate command to start the air purification units $PU_1$, $PU_2$, $PU_3$, $PU_4 \ldots PU_N$ in that specific locality.

The transmitter component 540 of processor component 500 is configured to transmit the said command to the controller 320 belonging to each of the air purification units $PU_1$, $PU_2$, $PU_3$, $PU_4 \ldots PU_N$ respectively. On receipt of the said command, the controller 320 of the air purification units $PU_1$, $PU_2$, $PU_3$, $PU_4 \ldots PU_N$ activates and runs the air purification units to give full throughput. By providing full throughput, it is meant that the air purification units are activated to their full capacity and multiple air purification units are activated so that the polluted air in a larger area can be cleaned and purified at a high speed so that less "operating time" is consumed in cleaning the air. Due to such less "operating time" of devices, the energy consumed is much lesser.

Each of the air purification units $PU_1$, $PU_2$, $PU_3$, $PU_4 \ldots PU_N$ comprises an air cleaning component 310.

In an embodiment, the air cleaning component 310 is selected from air filtration components such as a wet scrubber, an electrostatic precipitator, a particulate filter, a catalytic filter, a cyclonic separator and a baghouse collector. The air cleaning component may also be some other air filtration component. The disclosed air filtration components should not be construed as limitation to the present invention.

The air cleaning component 310 is adapted to clean the polluted air and release the clean air into the atmosphere.

Figures 5A, 5B:
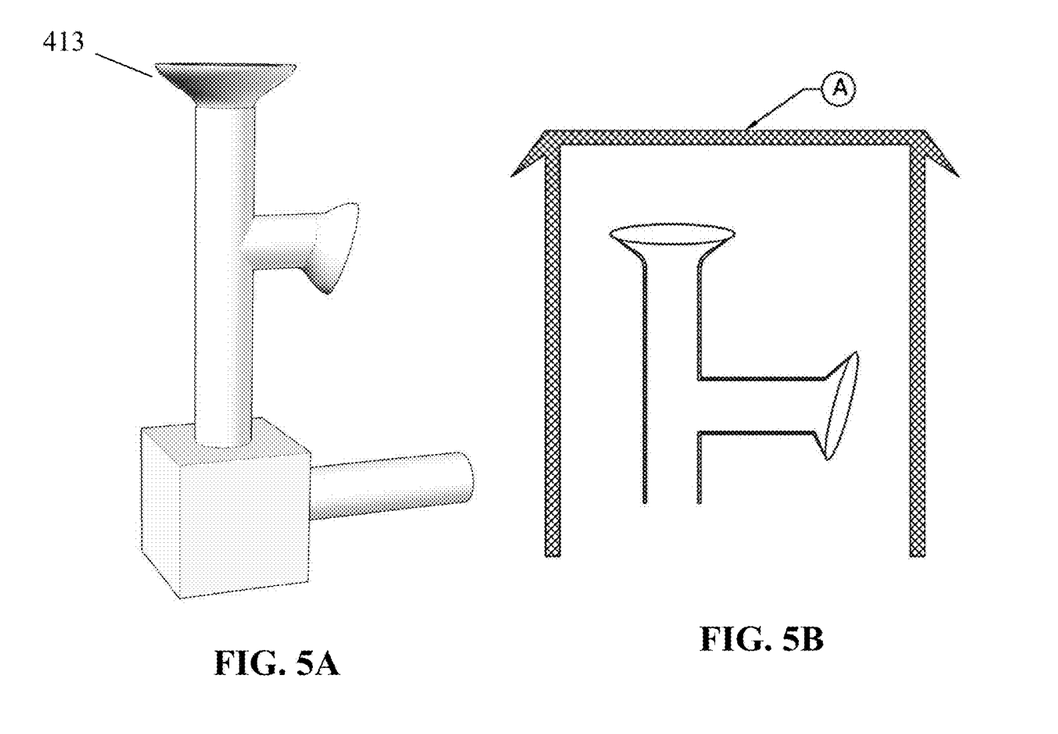
FIG. 5A illustrates the Perspective view of the suction vents for sucking in the polluted air from the outside atmosphere, according to various embodiments of the present invention.
FIG. 5B illustrates the Front Cross sectional view of the suction vents for sucking in the polluted air from the outside atmosphere, according to various embodiments of the present invention.

In an embodiment, the air purification system 100 comprises suction vents (as shown in FIG. 5A). The suction vents are capable of sucking in the polluted air from its surrounding area. The design of the suction vent has been shown in FIG. 5A. These suction vents begin sucking the polluted air from its surrounding once the air purification unit is activated to purify the polluted air in its surrounding location. The physical construction of the suction vents and its various views will be explained later in the description.

Figure 6A:
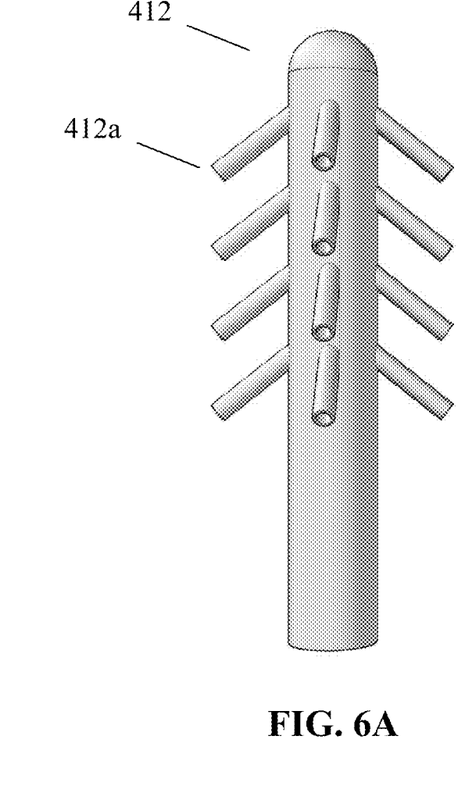
FIG. 6A illustrates the Front view of the air vents responsible for releasing the clean air in the outer atmosphere, according to various embodiments of the present invention.

In the embodiment, the air purification system 100 comprises air vents (as shown in FIG. 6A). These air vents are connected to the air purification units for releasing clean air into the surrounding atmosphere. The construction of the air vents and its various views will be explained later in the description.

Referring again to FIG. 2A, in the method 200, at step 208, if the air quality data is not 2 times of the preset clean air data or worse, the method 200 moves to step 212 where the analyzer module is adapted to further check if the air quality data is 1 times of the preset clean air data.

At step 212, if the analyzer module analyzes that the air quality data is 1 times of the preset clean air data or worse, then the method moves to step 216. At step 216, the analyzer module is adapted to generate a command for partial throughput such that this command is transmitted over to the controller 320 of each of the air purification units $PU_1$, $PU_2$, $PU_3$, $PU_4 \ldots PU_N$. Once the controller 320 receives the command, it activates each of the air purification units $PU_1$, $PU_2$, $PU_3$, $PU_4 \ldots PU_N$ for a specified and limited time period T1 which is based upon the air pollution trend data during the past in that location.

It will be obvious to a person skilled in the art that air pollution trend data relates to the historical data of air pollution at a specific location gathered for a longer period of time, for example, pollution trend for a year. The present system is adapted to analyze the period T1, for which the air purification unit is required to be activated so that the air gets purified for the specific location in minimal time period. By placing a limit on the time of operation, energy efficiency is realized for the operation of these air purifiers.

At step 218, the analyzer module is adapted to again check the current air quality data and compare it with the preset clean air data. If the current air quality data is better than 1 times the preset clean air data, then the method moves to step 220 and the analyzer module is adapted to generate a command to stop the corresponding air purification units.

If the analyzer module analyzes that the current air quality data is not better than 1 times of the preset clean air data, then the method 200 moves to step 222 where the analyzer module generates a command to run the air purification units in a particular location at full throughput at a limited time T2 on the basis of pollution trend data of that location. Thereafter the method 200 returns to the step 202 where the air quality of a particular location is monitored and the air pollutant data is generated via an air pollution monitoring unit. The method again follows the remaining steps in the flow chart as explained in the diagrams FIG. 2A and FIG. 2B. This "loop" is followed until the air quality is within the acceptable target or the "preset clean air data".

Referring again to the step 214, if the analyzer module analyzes that the air quality data is not worse than 1 times the preset clean air data, and then the analyzer module generates a command for stopping the air purification process. This command is then transmitted over to the controller 320 of each of the air purification units $PU_1$, $PU_2$, $PU_3$, $PU_4$ ... $PU_N$. Once the controller 320 receives the command, it stops each of the air purification units $PU_1$, $PU_2$, $PU_3$, $PU_4$ ... $PU_N$.

Figure 5C:
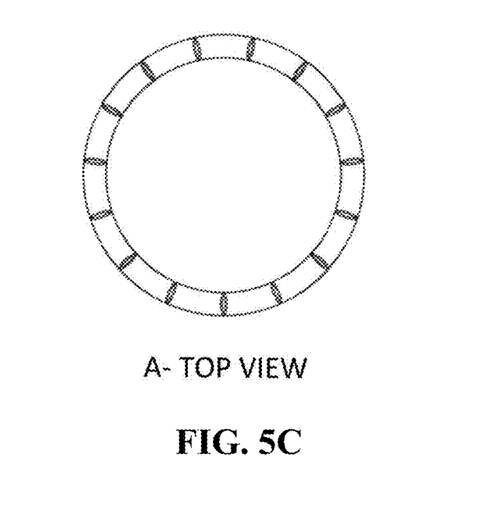
FIG. 5C illustrates the Top view of the suction vents for sucking in the polluted air from the outside atmosphere, according to various embodiments of the present invention.

Referring now to FIGS. 5A, 5B and 5C, there are shown various views of the suction vents 413 installed at each of the air purification units $PU_1$, $PU_2$, $PU_3$, $PU_4$ ... $PU_N$. These suction vents 413 are adapted to suck in the polluted air from the surrounding atmosphere when the air purification units $PU_1$, $PU_2$, $PU_3$, $PU_4$ ... $PU_N$ are activated. FIG. 5A provides a 3D perspective view of the suction vent 413 which has two suction inlets, one at the top and the other at the middle. The suction vent 413 is designed so that it sucks in an efficient quantity of polluted air.

In an embodiment, the suction vents 413 has an air flow control valve (not shown in the figure) which is capable of controlling the flow of air towards the air purification device so that the amount of polluted air being fed to the air purification device is in the appropriate quantity. This enhances the percentage of purification of the polluted air in an energy efficient manner.

The suction vents 413 are connected to the air purification units $PU_1$, $PU_2$, $PU_3$, $PU_4$ ... $PU_N$ provided with a Protective Casing A (cross-sectional view as shown in FIG. 5B) that protects the suction vents from sucking in waste materials like debris, scrap and other wastes from its surroundings.

FIG. 5C provides the top view of the Protective Casing A having a circular structure and solid from top. The top structure of the casing A is made of solid and strong material so that it remains intact in worse natural situations like heavy rain, low pressure, etc.

In an embodiment, as illustrated in FIG. 6A, there is shown a perspective view of the air vent 412 which are installed at different locations. The air vent 412 acts as an output or discharge vent for releasing out the fresh and purified air into the atmosphere. The air vent 412 comprises smaller air vents 412a at equal distances so that the clean air is distributed evenly into the atmosphere.

Figure 6B:
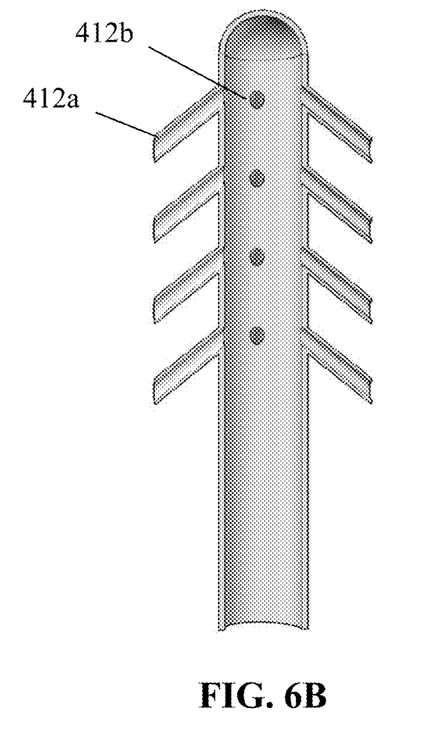
FIG. 6B illustrates the Front Cross Sectional view of the air vents responsible for releasing the clean air in the outer atmosphere, according to various embodiments of the present invention.

In this embodiment, as illustrated in FIG. 6B, the cross sectional view of the air vent 412 is seen. There is shown perforation 412b which leads way to the smaller air vents 412a.

Figure 6C:
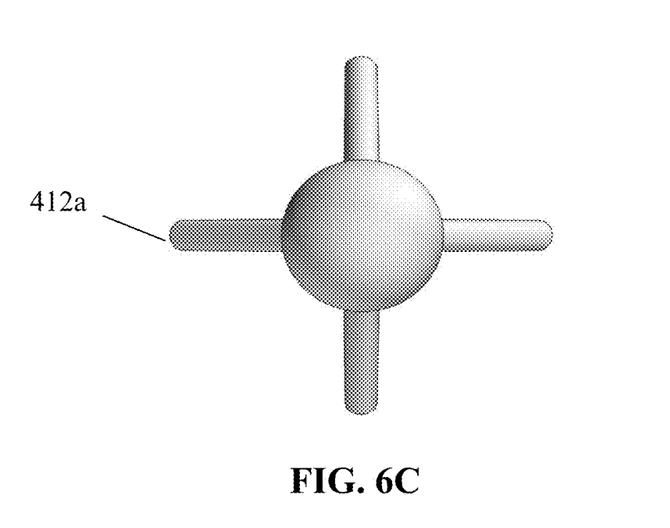
FIG. 6C illustrates the Top view of the air vents responsible for releasing the clean air in the outer atmosphere, according to various embodiments of the present invention.

In this embodiment, as illustrated in FIG. 6C, shows the 3D top view of the air vent 412 which is hemispherical and has solid structure. The top of the air vent is designed so that in any kind of climate change such as heavy rainfall, winter, summers, the air vent does not wear out or break. The flow of clean air from the air vents is towards the downward direction. The tilting of the smaller vents 412a is also towards the ground and the top of the air vent 412 is sealed so that any kind of waste material, debris or any sort of garbage does not enter into these smaller air vents 412a.

Figure 4:
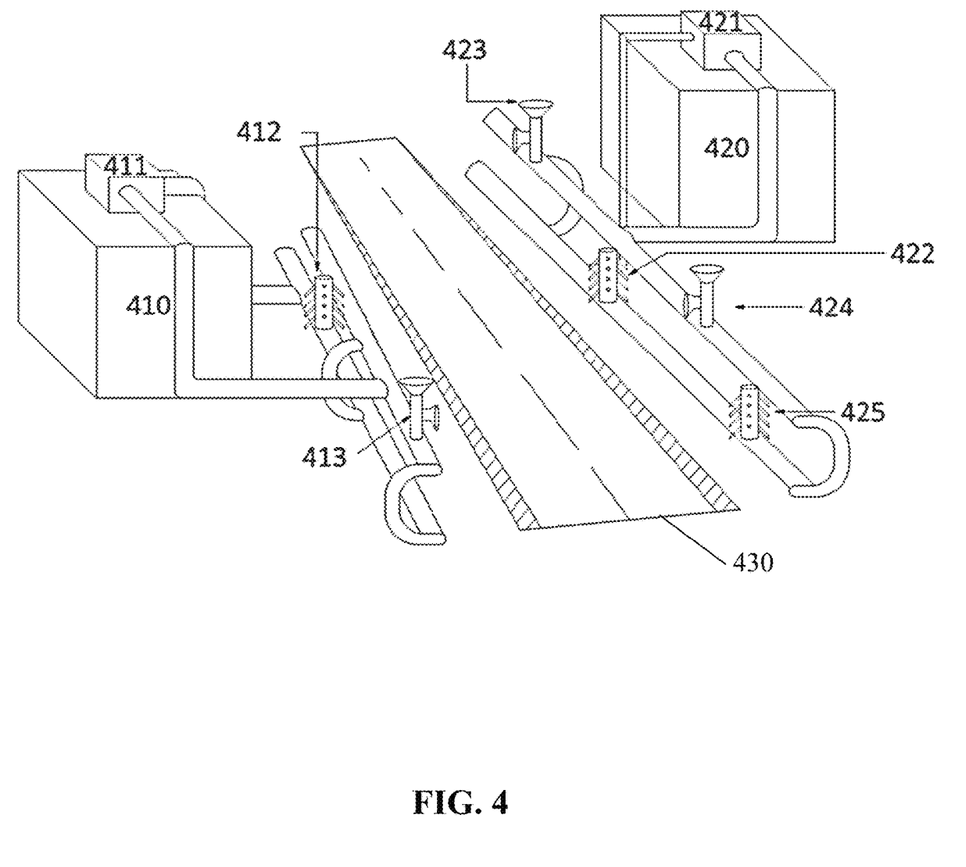
FIG. 4 illustrates a real time implementation of the said air purification system in a real time scenario, according to various embodiments of the present invention.

Referring now to FIG. 4 of the accompanying drawings, there is shown a real time implementation of the said air purification system. In the said FIG. 4, there is shown a road 430 meant for transportation by public. It will be obvious to a person skilled in the art that on the road 430 there will be a lot of transportation by cars, trucks and other vehicles which are considered as rich source for emitting pollutants into the atmosphere. Furthermore, there will also be pedestrians who would be walking on the footpaths and are subjected to inhaling the pollutants from their ambient atmosphere.

As shown in the FIG. 4, the constructed structures 410 and 420 are meant for the installation of the air pollution monitoring units $MU_1$, $MU_2$, $MU_3$, $MU_4$ ... $MU_N$ and air purification units $PU_1$, $PU_2$, $PU_3$, $PU_4$, ... $PU_N$. Alternatively, the Air Purification Units $PU_1$, $PU_2$, $PU_3$, $PU_4$ ... $PU_N$ may either be installed in basements of buildings constructed near roads or installed in underground housings to prevent ambient noise from reaching the public. Such an installation will be relatively more secure thus preventing unauthorized operation or safety issues.

There are shown identical suction vents 413, 423, 424 which are adapted to take in the polluted air from the surrounding atmosphere. These suction vents are connected to the air purification units $PU_1$, $PU_2$, $PU_3$, $PU_4$ ... $PU_N$. The protective enclosures surrounding these vents are not depicted in the FIG. 4 for purposes of clarity in the complex diagram.

There are shown identical air vents 412, 422, 425 which are adapted to release the fresh and clean air into the atmosphere. Note that the protective enclosures surrounding these vents are not shown in the FIG. 4 for purposes of clarity.

The structures 411, 421 represent the air purification units for taking in the polluted air which is inhaled through the suction units 413, 423, 424. Thereafter, the air purification units remove the pollutants and release the clean air via the air vents 412 and 422. Furthermore, these air purification units are controlled via the automated control unit 500 (not shown in FIG. 4).

In an embodiment, the physical configuration and installation of the suction vents and the air vents are split type configuration. Each suction vent and each respective air vent are installed at specific distance from each other. Such split type configurations of the vents ensure that the suction vents do not suck in the clean air released by the air vents. In addition, the split design ensures that the air purification units PU1, $PU_2$, $PU_3$, $PU_4$, ... , $PU_N$ are distantly located and/or separated from suction vents and discharge air vents. The design ensures benefits such as decreased ambient noise during operation of the air purification units, safer operation and protection of assets.

The present invention finds wide industrial applicability and has been invented to benefit the mankind. The air purification system is suitable for installation in highly polluted cities so that people residing in such polluted cities are relieved from inhaling the polluted air.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

What is claimed is:

1. An energy efficient air purification system for purifying a complex polluted environmental air condition at a specific location, the said air purification system comprising:
   a plurality of air pollution monitoring units installed at distant locations, wherein each of the said plurality of air pollution monitoring units are adapted for monitoring the air quality of its surrounding location;
   a plurality of air purification units installed at distant locations, wherein each of the said plurality of air purification units are adapted for purifying the polluted air of its surrounding location; and
   an automated centralized control unit working in communication with the said plurality of air pollution monitoring units and the said plurality of air purification units, wherein the said automated centralized control unit remotely controls the working of the said plurality of air purification units, the said automated centralized control unit including
      a data decoder adapted to decode a message format of an air pollutant data into the data format, and
      an analyzer module adapted to analyze the said data format in relation with the said preset clean air data of the specific location,
      wherein the analyzer module generates a command to operate the said plurality of air purification units at the specific location as per the said data analysis.

2. The energy efficient air purification system as claimed in claim 1, wherein each of the said plurality of air pollution monitoring units comprises:
   at least an air pollutant detector adapted to detect the level of at least one air pollutant to generate the air pollutant data;
   a processor adapted to process the said air pollutant data as detected by the said air pollutant detector into the said message format; and
   a communication interface having a transceiver adapted to transmit the said message format to the automated centralized control unit.

3. The energy efficient air purification system as claimed in claim 2, wherein at least an air pollutant detector is selected from an air particulate matter detector, a sulfur oxide detector, a carbon monoxide detector, a nitrogen oxide detector, a nitrogen dioxide detector, a smoke detector and any such detector capable of detecting pollutants into the air.

4. The energy efficient air purification system as claimed in claim 1, wherein each of the said plurality of air purification units comprises:
   at least an air cleaning component adapted to filter at least an air pollutant; and
   a controller working in communication with the said automated centralized control unit, wherein the said controller is adapted to control the functionality of each of the said plurality of air purification units.

5. The energy efficient air purification system as claimed in claim 4, wherein the said air cleaning component is selected from one of a wet scrubber, an electrostatic precipitator, a particulate filter, a catalytic filter, a cyclonic separator, a baghouse collector.

6. The energy efficient air purification system as claimed in claim 1, wherein the automated centralized control unit comprises a receiver component, a memory component, a processor component, and a transmitter component.

7. The energy efficient air purification system as claimed in claim 6, wherein the said receiver component is adapted to receive the said message format from the said communication interface.

8. The energy efficient air purification system as claimed in claim 6, wherein the said memory component is adapted to store the preset clean air data of the specific location, and a historical air quality data of the specific location.

9. The energy efficient air purification system as claimed in claim 6, wherein the said processor component comprises the said data decoder and the said analyzer module.

10. The energy efficient air purification system as claimed in claim 6, wherein the said transmitter component is adapted to transmit the said command to the controller.

11. An energy efficient air purification process for purifying a complex polluted environmental air condition at a specific location, the said air purification process comprises:
   monitoring the air quality of a plurality of distant locations via a plurality of air pollution monitoring units;
   generating an air pollutant data via each of the said plurality of air pollution monitoring units;
   processing the said air pollutant data into a message format corresponding to each of the said plurality of air pollution monitoring units;
   transmitting the said message format corresponding to each of the said plurality of air pollution monitoring units to an automated centralized control unit;
   comparing said message format corresponding to each of the said plurality of air pollution monitoring units with a preset clean air data of the specific location present on a memory component of the said automated centralized control unit; and
   generating and transmitting a command via the said automated centralized control unit to operate a plurality of air purification units.

12. The energy efficient air purification process as claimed in claim 11, wherein the air quality of a plurality of distant locations is monitored via at least an air pollutant detector selected from an air particulate matter detector, a sulfur oxide detector, a carbon monoxide detector, a nitrogen oxide detector, a nitrogen dioxide detector, a smoke detector and any such detector capable of detecting pollutants in the air.

13. The energy efficient air purification process as claimed in claim 11, wherein the said air pollutant data is processed into a message format via a processor each configured within the said plurality of air pollution monitoring units.

14. The energy efficient air purification process as claimed in claim 11, wherein the said message format is transmitted via a transceiver of a communication interface each configured within the said plurality of air pollution monitoring units.

15. The energy efficient air purification process as claimed in claim 11, wherein the said message format is received by a receiver component of the said automated centralized control unit and transferred to a processor component of the said automated centralized control unit.

16. The energy efficient air purification process as claimed in claim 15, wherein the said processor component is adapted to decode the said message format into a data format via a data decoder present thereon, and analyze the said data format via an analyzer module in relation with the said preset clean air data of the specific location, wherein the analyzer module generates a command as per the said data analysis.

17. The energy efficient air purification process as claimed in claim 16, wherein the said command is transmitted via a transmitter component of the automated centralized control unit to operate a controller each present on a plurality of air purification units.

18. The energy efficient air purification system as claimed in claim 9, wherein the analyzer module is adapted to generate the command to operate the said plurality of air purification units at the specific location when the air quality data is more than 2 times the preset air clean data at the said specific location.

19. The energy efficient air purification system as claimed in claim 18, wherein the controller of each of the said air purification units is adapted to activate and run the said plurality of air purification units to give full throughput.

20. The energy efficient air purification system as claimed in claim 18, wherein the analyzer module is adapted to check if the air quality data is equal to or more than 1 times of the preset clean air data and less than 2 times of the preset clean air data, and on basis of this analysis, the analyzer module generates the command to operate the said plurality of air purification units to give partial throughput at the specific location.

* * * * *